(12) United States Patent
Kim et al.

(10) Patent No.: US 10,281,379 B2
(45) Date of Patent: May 7, 2019

(54) NANO MATERIAL TESTING APPARATUS AND METHOD FOR TESTING MATERIAL USING THE SAME

(71) Applicant: UNIST(ULSAN NATIONAL INSTITUTE OF SCIENCE AND TECHNOLOGY), Ulsan (KR)

(72) Inventors: Ju Young Kim, Ulsan (KR); Young Cheon Kim, Ulsan (KR); Si Hoon Kim, Ulsan (KR)

(73) Assignee: UNIST(ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 130 days.

(21) Appl. No.: 15/372,354

(22) Filed: Dec. 7, 2016

(65) Prior Publication Data

US 2017/0363523 A1    Dec. 21, 2017

(30) Foreign Application Priority Data

Jun. 15, 2016   (KR) .................. 10-2016-0074575

(51) Int. Cl.
*H04N 5/247*   (2006.01)
*G01N 3/06*   (2006.01)
*G01N 3/08*   (2006.01)
*G01N 3/20*   (2006.01)

(52) U.S. Cl.
CPC ............. *G01N 3/068* (2013.01); *G01N 3/08* (2013.01); *G01N 3/20* (2013.01); *H04N 5/247* (2013.01); *G01N 2203/0286* (2013.01)

(58) Field of Classification Search
CPC .. G01N 3/068; G01N 2203/0647; G01N 3/08; G01N 3/20; G01N 2203/0016; G01N 2203/0017; G01N 2203/0019; H04N 5/247
See application file for complete search history.

(56) References Cited

U.S. PATENT DOCUMENTS 4,426,875 A * 1/1984 Crosby, Jr. ............... G01N 3/08
                                                         73/12.13
4,690,001 A * 9/1987 Harvey .................... G01D 5/34
                                                         348/294

(Continued)

FOREIGN PATENT DOCUMENTS

CN          205580873 U  *  9/2016
JP          2004-205248 A     7/2004
(Continued)

*Primary Examiner* — David E Harvey
(74) *Attorney, Agent, or Firm* — Revolution IP, PLLC

(57) ABSTRACT

A nano material testing apparatus includes a main frame; a testing unit including an actuator and a load cell connected to the actuator; a jig unit configured to be connected to the testing unit and including an upper jig that clamps one side of an upper portion of the nano material specimen and a lower jig that is located below the upper jig and clamps one side of a lower portion of the nano material specimen; a stage unit configured to be connected to the lower jig; a first alignment unit configured to be located to be spaced apart from a front surface of the nano material specimen; a second alignment unit configured to be located to be spaced apart from side surfaces of the nano material specimen; and a controller.

8 Claims, 5 Drawing Sheets

(56) References Cited

U.S. PATENT DOCUMENTS

| | | | | |
|---|---|---|---|---|
| 4,841,779 A * | 6/1989 | Mitsuhashi | G01B 11/16 | 73/826 |
| 6,332,364 B1 * | 12/2001 | Buschmann | G01N 3/08 | 73/788 |
| 7,258,022 B2 * | 8/2007 | Wenski | G01N 3/08 | 73/800 |
| 7,681,459 B1 * | 3/2010 | Yang | G01N 3/08 | 73/760 |
| 8,297,130 B2 * | 10/2012 | Wheeler, IV | G01N 1/2226 | 73/818 |
| 2003/0152194 A1 * | 8/2003 | Nordmeyer | B01L 9/065 | 378/73 |
| 2003/0182069 A1 * | 9/2003 | Banes | G01N 3/068 | 702/33 |
| 2004/0153292 A1 * | 8/2004 | Hay | G01N 3/068 | 702/189 |
| 2006/0186874 A1 * | 8/2006 | Mackin | G01N 3/42 | 324/754.1 |
| 2010/0186520 A1 * | 7/2010 | Wheeler, IV | G01N 1/2226 | 73/818 |
| 2012/0287248 A1 * | 11/2012 | Erdman, III | G01N 3/068 | 348/47 |
| 2013/0042696 A1 * | 2/2013 | Fukuda | G01N 3/04 | 73/800 |
| 2013/0056905 A1 * | 3/2013 | Hamaya | G03F 7/0002 | 264/293 |
| 2013/0192383 A1 * | 8/2013 | Reed | G01N 3/08 | 73/818 |
| 2017/0322129 A1 * | 11/2017 | Wenski | G01N 3/068 | |

FOREIGN PATENT DOCUMENTS

| | | |
|---|---|---|
| JP | 3131611 U | 5/2007 |
| KR | 10-0613726 B1 | 8/2006 |
| WO | WO 01/18555 A1 * | 3/2001 |
| WO | WO 2015/055795 A1 * | 4/2015 |

* cited by examiner

NANO MATERIAL TESTING APPARATUS AND METHOD FOR TESTING MATERIAL USING THE SAME

CROSS REFERENCE TO PRIOR APPLICATIONS

This application claims the benefit of Korean Patent Application No. 10-2016-0074575 filed on Jun. 15, 2016, in the Korean Intellectual Property Office, the disclosure of which is incorporated herein in its entirety by reference.

TECHNICAL FIELD

The present invention relates to a nano material testing apparatus and a method for testing a material using the same, and more particularly, to a nano material testing apparatus that checks mechanical properties of a nano-scale material and a method for testing a material using the same.

BACKGROUND ART

In general, there are material testing apparatuses for checking characteristics of a material. These material testing apparatuses are used as apparatuses for checking various mechanical characteristics by tensioning or pressing a specimen of a material.

In particular, a tension test using the material testing apparatus is a method for obtaining an elastic modulus, a breaking strength, etc. using direct property values. In particular, because experiments of a material, such as a micro or nano-scale metal and a polymer, cannot be carried out using a general bulk-scale material testing apparatus, a micro tension testing apparatus or nano testing apparatus is used.

That is, the above-described tension tests are carried out by a subminiature material testing apparatus (a tension testing apparatus) for measuring mechanical properties of a product and a material that require a very small load. In particular, because, in a nano tension test, mechanical characteristics of the product can be precisely measured in nano units, mechanical characteristics of a material and a product developed using a nano technology can be precisely measured in nano units such that the nano tension test is suitable for measurement of the mechanical characteristics of the material and the product developed using the nano technology.

Meanwhile, because a material testing apparatus for checking nano characteristics mounts a very small specimen, unlike in a conventional material testing apparatus, a mounting method thereof is somewhat difficult. Thus, in order to relieve these difficulties, Korean Patent Registration No. 613726 discloses a specimen mounting apparatus for a tension testing apparatus configured to fix both ends of a sample tensioned by a driving force from a driving apparatus to a moving stage side and a clamp side, respectively, the specimen mounting apparatus including a grip table having an end disposed in the middle between the moving stage side and the clamp side and a gripping means that operates in a width direction of a grip.

However, in a conventional nano material testing apparatus, it is not easy to mount a specimen having a small size and thus, causes a difficulty in carrying out a test. In addition, because the specimen cannot be mounted only in a horizontal direction, only the tension test can be carried out such that various tests including tension, compression, bending, etc. cannot be carried out.

DETAILED DESCRIPTION OF THE INVENTION

Technical Problem

The present invention provides a nano material testing apparatus capable of easily mounting a nano-scale specimen and carrying out a compression test and a bending test in addition to a tension test so that various properties of the nano specimen can be measured, and a method for testing a material using the same.

Technical Solution

According to an aspect of the present invention, there is provided a nano material testing apparatus including: a main frame; a testing unit including an actuator coupled to an upper portion of the main frame and generating displacement of a nano material specimen and a load cell connected to the actuator; a jig unit configured to be connected to the testing unit and including an upper jig that clamps one side of an upper portion of the nano material specimen and a lower jig that is located below the upper jig and clamps one side of a lower portion of the nano material specimen; a stage unit configured to be connected to the lower jig, to support the lower jig in an upward direction, to be moved in a multi-axis direction and to make the lower jig to be moved in the multi-axis direction; a first alignment unit configured to be located to be spaced apart from a front surface of the nano material specimen, to provide an image of the front surface of the nano material specimen and to allow alignment in a direction of the front surface of the nano material specimen to be checked through the front surface image of the nano material specimen; a second alignment unit configured to be located to be spaced apart from side surfaces of the nano material specimen, to provide an image of the side surfaces of the nano material specimen and to allow alignment in a direction of the side surfaces of the nano material specimen to be checked through the side surface image of the nano material specimen; and a controller configured to process signals received from the load cell and to drive and control the actuator and the stage.

According to another aspect of the present invention, there is provided a method for testing a material using the nano material testing apparatus, the method including: mounting the nano material specimen on the specimen auxiliary fixing device; moving the stage unit to move the lower jig to the specimen auxiliary fixing device and then, moving the nano material specimen to the lower jig, mounting the nano material specimen on the lower jig, and moving the stage unit so that the lower jig is moved to be below the upper jig, wherein the moving, the moving, the mounting, and the moving are performed by the worker; checking alignment of the nano material specimen using the first alignment unit and the second alignment unit to adjust a position of the nano material specimen; mounting the nano material specimen on the upper jig in a state in which the load cell protection device is connected to the upper jig; separating the load cell protection device from the upper jig and then carrying out a test by moving the actuator; and measuring a change in the nano material specimen using information received from the first alignment unit, the second alignment unit, and the load cell during a test.

Effect of the Invention

A nano material testing apparatus and a method for testing a material using the same according to the present invention have the following effects.

First, a nano-scale specimen can also be easily mounted, and a compression test and a bending test in addition to a tension test can be carried out so that various properties of the nano specimen can be measured.

Second, images are measured in two directions of a nano material specimen using a first alignment unit and a second alignment unit so that alignment of the nano material specimen can be precisely and easily performed.

Third, the length of the nano material specimen and a change in a thickness direction thereof can be measured in real time during a test using the first alignment unit and the second alignment unit, and furthermore, a change in the length and the thickness of the nano material specimen and a change in surface caused by deformation of the specimen can be simultaneously measured.

Fourth, mounting of the nano material specimen of which direct handling is difficult, can be easily performed using a specimen auxiliary fixing device.

Fifth, a heating portion and a chamber are mounted on a jig unit so that a test can be carried out while a high-temperature and humidity environment can be selectively established.

Sixth, no excessive load is applied to a load cell when the nano material specimen is mounted, using a load cell protection device so that damage of the load cell can be prevented.

MODE OF THE INVENTION

Hereinafter, exemplary embodiments of the present invention will be described in detail with reference to the accompanying drawings.

Figure 1:
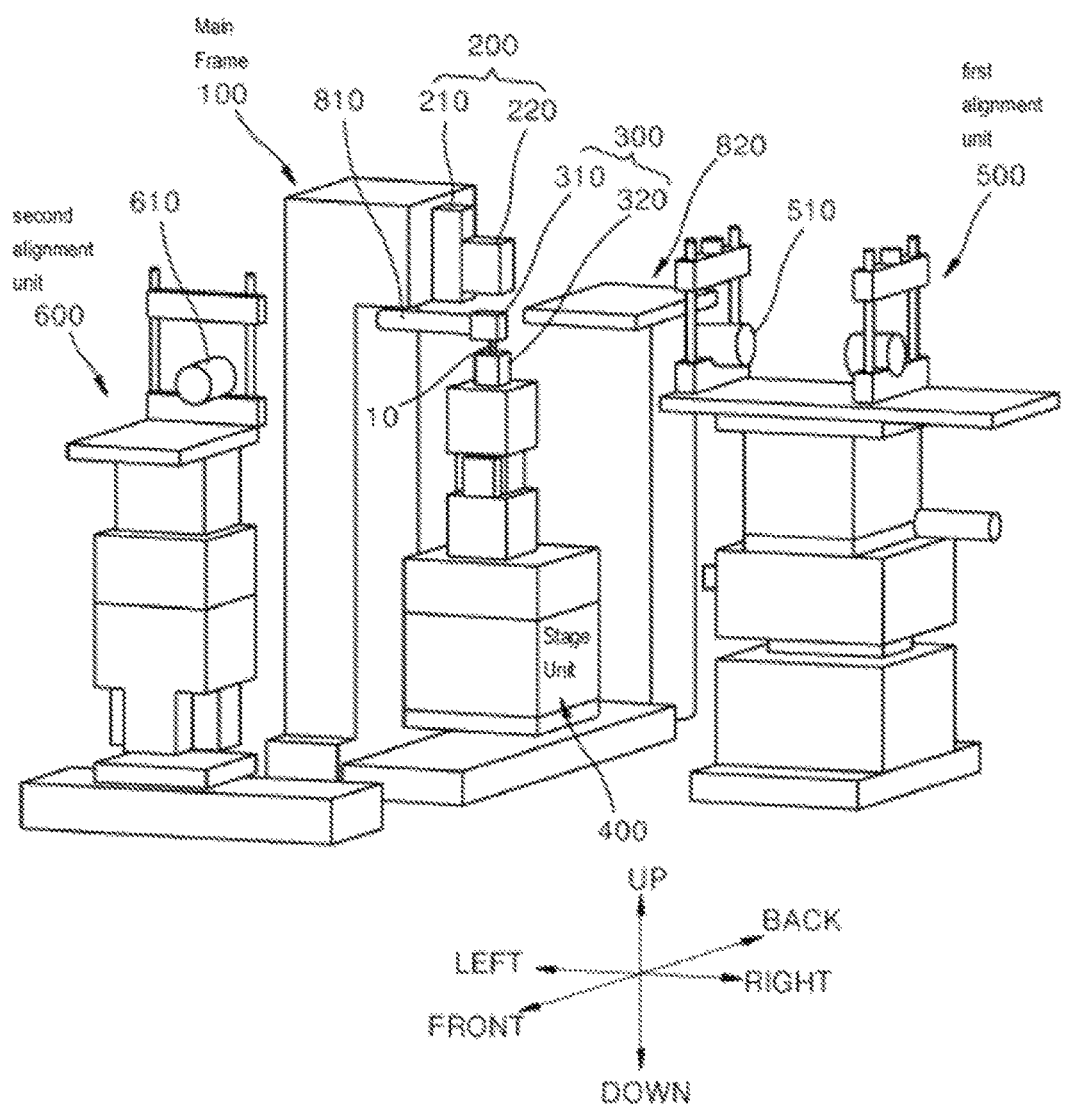
FIG. 1 is a perspective view of a nano material testing apparatus according to an embodiment of the present invention.
Figure 2:
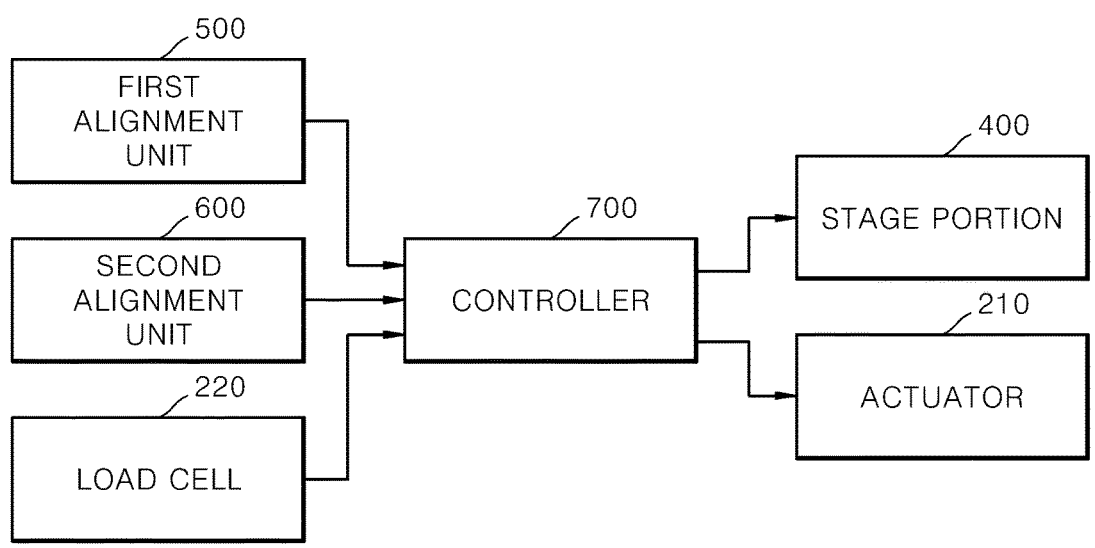
FIG. 2 is a block diagram of a control flow of a controller of the nano material testing apparatus illustrated in FIG. 1.
Figure 3:
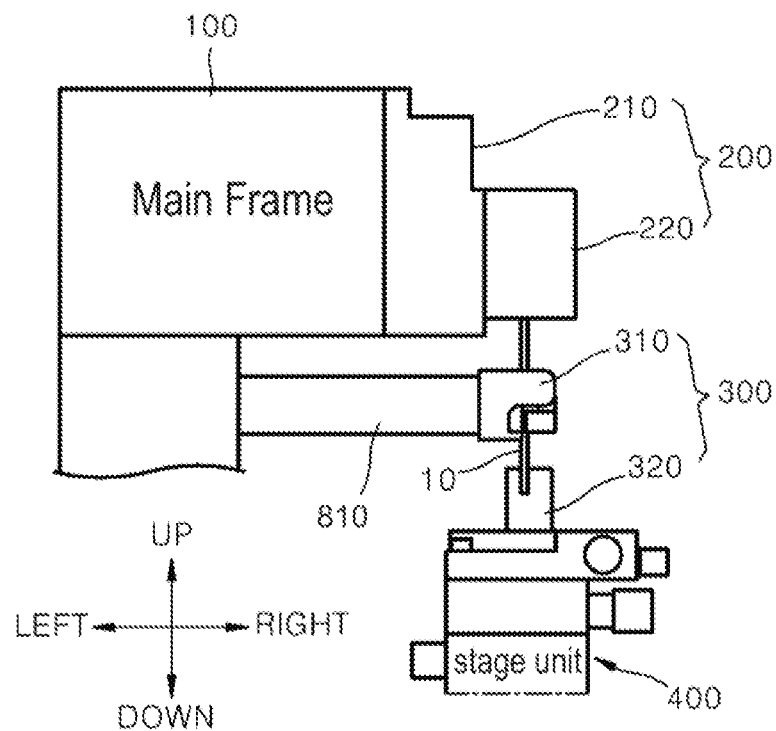
FIG. 3 is a view of a jig unit of the nano material testing apparatus of FIG. 1.

First, referring to FIG. 1, a nano material testing apparatus according to an embodiment of the present invention, which is used to check mechanical characteristics of a nano-scale nano material specimen 10 at a level of mm or less to be attached to a jig unit 300, includes a main frame 100, a testing unit 200, the jig unit 300, a stage unit 400, a first alignment unit 500, a second alignment unit 600, and a controller 700.

The main frame 100 stands in a direction perpendicular to an experiment bed and supports the entire structure of the nano material testing apparatus.

The testing unit 200 includes an actuator 210 that is coupled to one side of an upper portion of the main frame 100 and generates displacement of the nano material specimen 10 so as to measure a tensile property of the nano material specimen 10, and a load cell 220 connected to the actuator 210. The actuator 210 and the load cell 220 are coupled to each other in a direction perpendicular to the upper portion of the main frame 100 so that various mechanical properties such as compression and bending in addition to the tensile property in a vertical direction can be measured using experiments.

A general linear actuator 210 may be used as the actuator 210 and may be configured of a piezo type actuator for small displacement. The load cell 220 is attached to an operating portion of the actuator 210, and preferably, the load cell 220 is located in the same line as that of the operating portion, but embodiments of the present invention are not limited thereto.

The jig unit 300 is connected to the testing unit 200, fixes the nano material specimen 10 in the standing state in the vertical direction, and includes an upper jig 310 and a lower jig 320.

The upper jig 310 clamps one side of the upper portion of the nano material specimen 10 and is detachably coupled to the testing unit 200 so that the upper jig 310 can be replaced with another one for each of a tension test, a compression test, and a bending test of the nano material specimen 10.

The lower jig 320 clamps one side of a lower portion of the nano material specimen 10 and is detachably coupled to the stage unit 400 so that the lower jig 320 can be replaced with another one for each of the tension test, the compression test, and the bending test of the nano material specimen 10.

Here, the upper jig 310 and the lower jig 320 each have a nut shape, and the testing unit 200 and the stage unit 400 each have a bolt shape so as to correspond to the upper jig 310 and the lower jig 320, respectively, so that the testing unit 200 and the stage unit 400 can be detachably coupled to each other. This is an exemplary embodiment, and it is obvious that various configurations may be applied to the above-described elements if the above-described objective of the present invention can be achieved through the above-described elements.

Here, a detailed configuration of the upper jig 310 and the lower jig 320 in the compression test and the bending test will be described below.

Meanwhile, the nano material testing apparatus may include a heating portion and an insulation portion, which are coupled to the upper jig 310 or the lower jig 320 or the upper jig 30 and the lower jig 320, respectively. The heating portion may heat the nano material specimen 10 at a set temperature using a temperature controlling device in response to temperature detected by a temperature sensor for detecting temperature of the nano material specimen 10, and the insulation portion cuts off heat conducted to the jig unit 300.

Furthermore, the nano material testing apparatus may include a humidity chamber capable of controlling and maintaining inside humidity by sealing the nano material specimen 10 and the jig unit 300 so that deformation of the nano material specimen 10 can be measured in a state in which humidity inside the humidity chamber is maintained at a constant level.

The stage unit 400 is connected to the lower jig 320, supports the lower jig 320 in an upward direction, is moved in a multi-axis direction, and makes the lower jig 320 to be moved in the multi-axis direction.

Here, the stage unit 400 is moved in forward/backward, left/right, and upward/downward directions and includes a first stage capable of supporting the lower jig 320 in the upward direction and being slightly moved in XYZR-axis directions and a tilt axis direction, and a second stage capable of supporting the first stage in the upward direction, including a lower rail stage and being roughly moved in XYZ-axis directions. However, this is an exemplary embodiment, and it is obvious that the stage unit 400 may have various configurations including a well-known rail type stage if the above-described objective of the present invention can be achieved through the stage unit 400.

The first alignment unit 500 is located to be spaced apart from a front surface of the nano material specimen 10, provides an image of the front surface of the nano material specimen 10, and allows alignment in a direction of the front surface of the nano material specimen 10 to be checked using the front surface image of the nano material specimen 10.

In detail, the first alignment unit 500 includes a first camera 510 for measuring the front surface image of the nano material specimen 10 in real time, a first measurement portion that is connected to the first camera 510 and provides a real-time front surface deformation image of the nano material specimen 10 in real time, and a first analyzing portion that is connected to the first measurement portion, analyzes the front surface image of the nano material specimen 10 in real time and measures a deformation rate of the nano material specimen 10 in its front surface direction.

The first alignment unit 500 may provide the image of the nano material specimen 10 in real time when the nano material specimen 10 attached to the lower jig 320 is mounted on the upper jig 310, so as to optimize alignment in the front surface direction and may measure a real-time deformation image during a tension test so that an accurate deformation rate can be obtained.

The second alignment unit 600 is located at one side of the main frame 100 to be spaced apart from side surfaces of the nano material specimen 10, provides an image of the side surfaces of the nano material specimen 10, and allows alignment in a direction of the side surfaces of the nano material specimen 10 to be checked using the side surface image of the nano material specimen 10.

In detail, the second alignment unit 600 includes a second camera 610 for measuring the side surface image of the nano material specimen 10, a second measurement portion that is connected to the second camera 610 and provides a real-time side surface deformation image of the nano material specimen 10, and a second analyzing portion that is connected to the second measurement portion, analyzes the side surface image of the nano material specimen 10 and measures a deformation rate of the nano material specimen 10 in the direction of the side surfaces of the nano material specimen 10.

The second alignment unit 600 provides an image in real time when a sample attached to the lower jig 320 is mounted on the upper jig 320 so that side surface alignment can be optimized and if necessary, a change in a thickness direction of the sample can be measured.

The first analyzing portion and the second analyzing portion may be independently installed at the first alignment unit 500 and the second alignment unit 600 or may be integrally installed at the controller 700.

A charge-coupled device (CCD) camera may be used as the first camera 510 and the second camera 610, respectively, and each of the first analyzing portion and the second analyzing portion may use a digital image correlation (DIC) analysis technique.

The controller 700 performs control and analysis of the entire device for a test of the nano material specimen 10 and processes signals received from the load cell 220 and the actuator 210 to drive and control the actuator 210 and the stage according to the signals. That is, the controller 700 calculates mechanical characteristics of the nano material specimen 10 based on the signals of the load cell 220 detected according to an operation of the actuator 210. In addition, the controller 700 receives the front surface image of the nano material specimen 10 provided by the first alignment unit 500 and the side surface image of the nano material specimen 10 provided by the second alignment unit 600 so as to check characteristics of the images of the nano material specimen 10.

Meanwhile, the nano material testing apparatus includes a load cell protection device 810 for protecting the load cell 220 when the nano material specimen 10 is mounted. The load cell protection device 810 may move forward/backward so that one side of the load cell protection device 810 can be coupled to the main frame 100 and the other side thereof can be selectively connected to the upper jig 310. The other side of the load cell protection device 810 moves forward so that no excessive load is applied to the load cell 220 while the nano material specimen 10 is clamped at the upper jig 310. Thus, the load cell protection device 810 is connected to the upper jig 310, and the other side of the load cell protection device 810 moves backward during a test.

In addition, the nano material testing apparatus includes a specimen auxiliary fixing device 820 that is located at the other side of the main frame 100 facing the second alignment unit 600 and selectively clamps the other side of the nano material specimen 10 by a worker's manipulation so as to fix the nano material specimen 10 before the nano material specimen 10 is mounted on the lower jig 320.

The specimen auxiliary fixing device 820 is used to mount the nano material specimen 10 of which direct handling is limited due to its small size, on the lower jig 320 and includes a tongs type fixing device (not shown) for fixing the nano material specimen 10 temporarily before the nano material specimen 10 is mounted on the lower jig 320.

Figure 4:
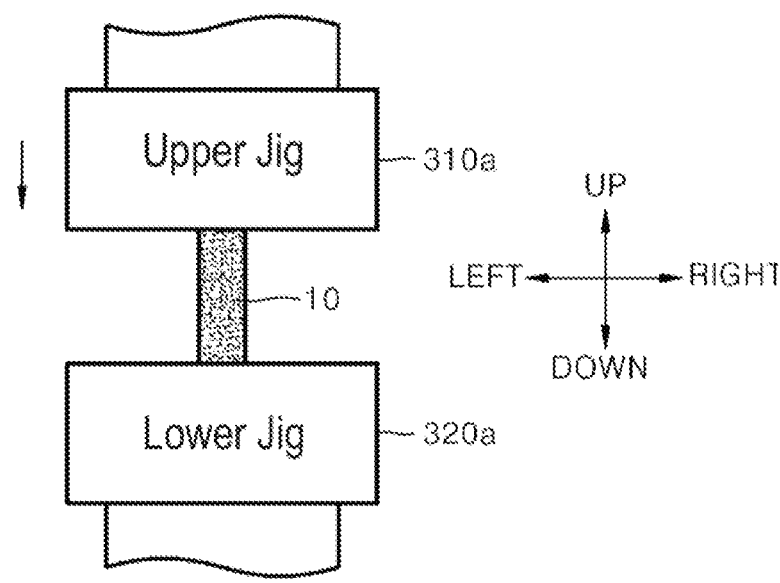
FIG. 4 is a view of the jig unit of the nano material testing apparatus of FIG. 1 during a compression test.

Meanwhile, the upper jig 310 and the lower jig 320 are configured to be replaced with another one so as to be used in each of the tension test, the compression test, and the bending test, as described above, so that each of the above-described tests can be carried out. In this regard, referring to FIG. 4, FIG. 4 illustrates a case where the compression test is carried out, and a contact surface between an upper jig 310*a* and a lower jig 320*a* that contact the nano material specimen 10 has a flat shape, and the nano material specimen 10 is inserted between a lower side surface of the upper jig 310*a* and an upper side surface of the lower jig 320*a*, and in this state, the upper jig 310*a* is moved in a downward direction so that a compression test of the nano material specimen 10 is carried out.

Figure 5:
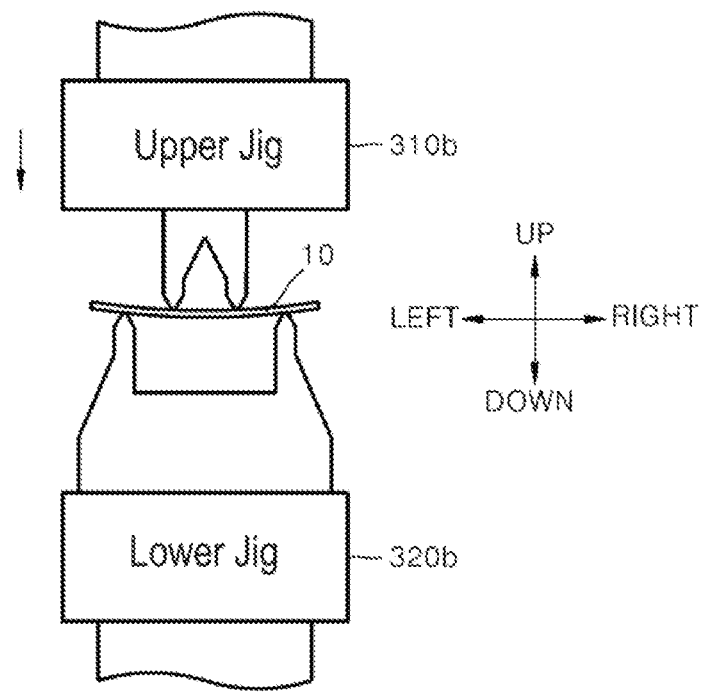
FIG. 5 is a view of the jig unit of the nano material testing apparatus of FIG. 1 during a bending test.
Figure 6:
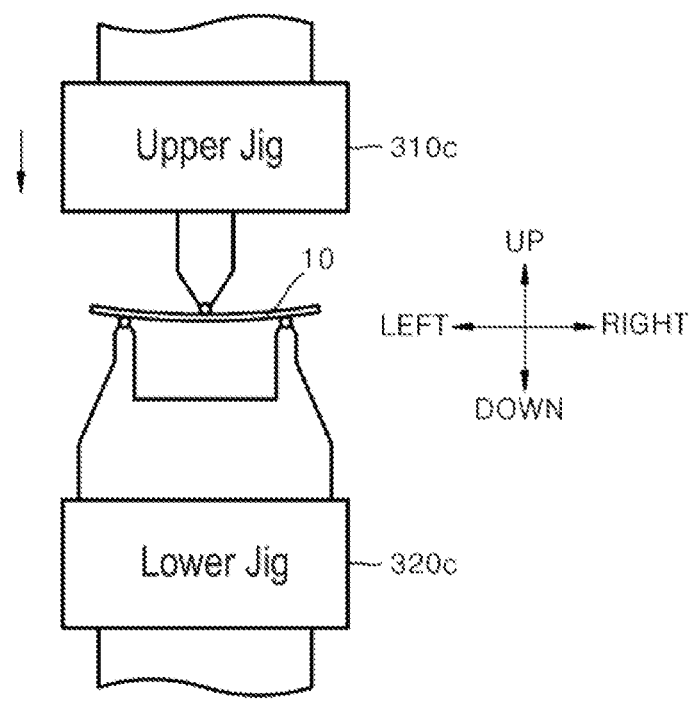
FIG. 6 is a view of the jig unit of FIG. 5 according to another embodiment.

Next, FIGS. 5 and 6 illustrate a case where a bending test is carried out, and a upper jig 310*b* and a lower jig 320*b* have various shapes including a three-point bending shape (see FIG. 5) and a four-point bending shape (see FIG. 6) according to the shape of a test specimen, and the upper jig 310*b* in a state in which a plate-shaped nano sample specimen is horizontally placed on a top surface of the lower jig 320*b*, is pressed onto a top surface of the nano material specimen 10 so that the nano material specimen can be bent.

As described above, in the nano material testing apparatus, mounting of the nano-scale nano material specimen 10 can be easily mounted in the vertical direction, and a compression test and a bending test in addition to a tension test can be carried out so that various properties of a nano material specimen can be measured and a change in the longitudinal direction and the thickness direction of a standard tension test specimen can be measured in real time.

Figure 7:
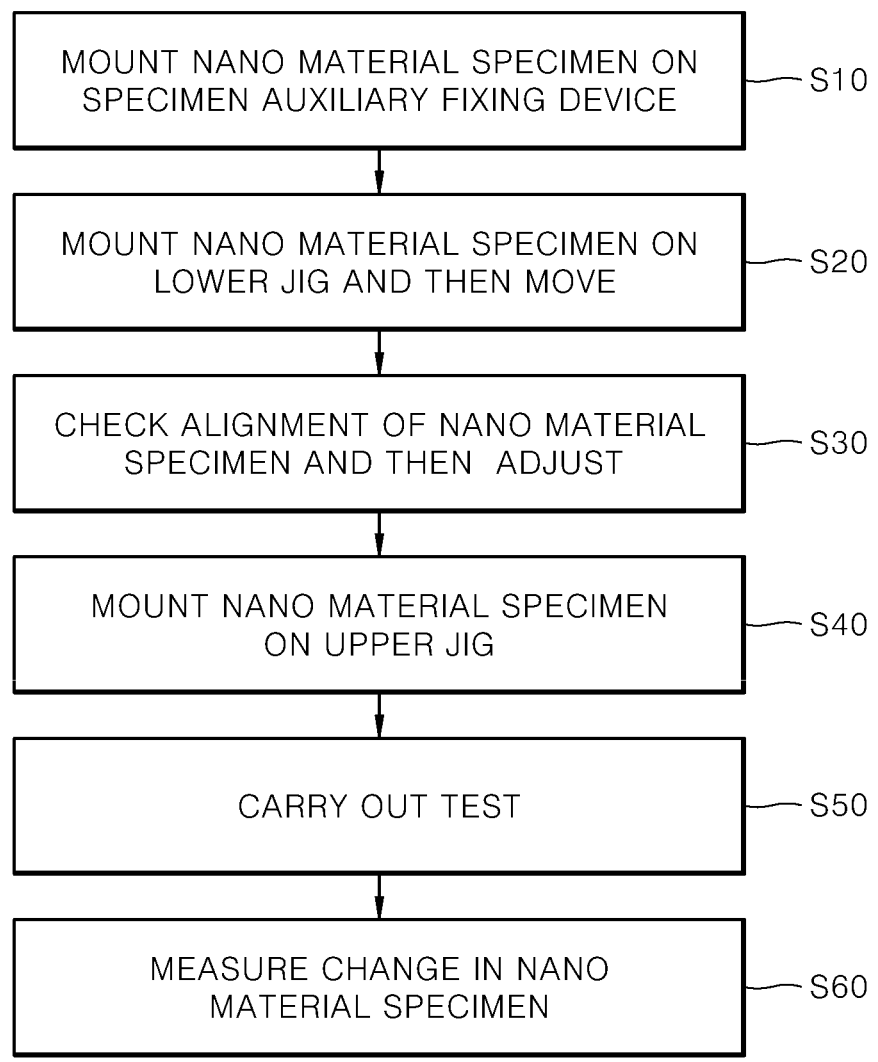
FIG. 7 is a flowchart illustrating a method for testing a material using the nano material testing apparatus of FIG. 1.

Hereinafter, a method for testing a material using the nano material testing apparatus will be described with reference to FIG. 7.

First, in order to mount a nano material specimen 10, the nano material specimen 10 is mounted on the specimen auxiliary fixing device 820 (S10).

Then, the worker moves the stage unit 400 on which the lower jig 320 is mounted, so as to move the lower jig 320 to the specimen auxiliary fixing device 820, and the specimen auxiliary fixing device 820 moves the nano material specimen 10 to the lower jig 320 so that the nano material specimen 10 can be mounted on the specimen auxiliary fixing device 820, and then the stage unit 400 is moved in such a way that the lower jig 320 is moved to be below the upper jig 310 (S20).

Then, alignment of the nano material specimen 10 is checked using the first alignment unit 500 and the second alignment unit 600 so that the position of the nano material specimen 10 is adjusted (S30).

After, in this way, the position of a lower portion of the nano material specimen 10 is adjusted, the nano material specimen 10 is mounted on the upper jig 310 in a state in which the load cell protection device 810 is connected to the upper jig 310 (S40). Here, the load cell protection device 810 moves forward/backward to be selectively connected to the upper jig 310, and the other side of the load cell protection device 810 moves forward so that no excessive load is applied to the load cell 220 while the nano material specimen 10 is clamped at the upper jig 310 and thus, the load cell protection device 810 is connected to the upper jig 310.

Subsequently, the load cell protection device 810 is separated from the upper jig 310 and then, the actuator 210 to which the load cell 220 is attached, is moved so that a tension test can be carried out (S50).

During the tension test, a local change in the nano material specimen 10 is observed using an image through information received from the first alignment unit, the second alignment unit, and the load cell 220 so that a deformation rate of the nano material specimen 10 can be measured (S60).

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

According to the present invention, the present invention can be used in a material testing apparatus for checking mechanical properties of a nano/micro-scale material, a tension testing apparatus, a compression testing apparatus, and a bending testing apparatus.

The invention claimed is:

1. A nano material testing apparatus comprising:
a main frame;
a testing unit comprising an actuator coupled to an upper portion of the main frame and generating displacement of a nano material specimen and a load cell connected to the actuator;
a jig unit being connected to the testing unit and comprising an upper jig that clamps one side of an upper portion of the nano material specimen and a lower jig that is located below the upper jig and clamps one side of a lower portion of the nano material specimen;
a stage unit connected to the lower jig supporting the lower jig in an upward direction, being moved in a multi-axis direction and enabling the lower jig to be moved in the multi-axis direction,
wherein the stage unit is moved in forward/backward, left/right, and upward/downward directions and comprises a first stage capable of supporting the lower jig in the upward direction and being slightly moved in XYZR-axis directions and a tilt axis direction, and a second stage capable of supporting the first stage in the upward direction and being moved in XYZ-axis directions;
a first alignment unit comprising a first camera and being separately disposed from the main frame, wherein the first camera is spaced apart from a front surface of the nano material specimen, provides an image of the front surface of the nano material specimen and allows alignment in a direction of the front surface of the nano material specimen to be checked through the front surface image of the nano material specimen;
a second alignment unit comprising a second camera and being separately disposed from the main frame, wherein the second camera is spaced apart from side surfaces of the nano material specimen, provides an image of the side surfaces of the nano material specimen and allows alignment in a direction of the side surfaces of the nano material specimen to be checked through the side surface image of the nano material specimen; and
a controller configured to process signals received from the load cell and to drive and control the actuator and the stage.

2. The nano material testing apparatus of claim 1, wherein the first camera provides a real-time front surface deformation image of the nano material specimen.

3. The nano material testing apparatus of claim 1, wherein the second camera provides a real-time side surface deformation image of the nano material specimen.

4. The nano material testing apparatus of claim 1, further comprising a load cell protection device movable in a forward/backward direction so that one side of the load cell protection device is coupled to the main frame and the other side of the load cell protection device is selectively connected to the upper jig, the other side of the load cell protection device moving forward in such a way that no excessive load is applied to the load cell while the nano material specimen is clamped at the upper jig and thus the load cell protection device is connected to the upper jig.

5. The nano material testing apparatus of claim 1, further comprising a specimen auxiliary fixing device disposed at one side of the main frame, selectively clamping the other side of the nano material specimen by a worker's manipulation so as to fix the nano material specimen temporarily before the nano material specimen is mounted on the lower jig.

6. The nano material testing apparatus of claim 1, wherein the upper jig clamps one side of an upper portion of the nano material specimen and is detachably coupled to the testing unit so that the upper jig is capable of being replaced with another one for each of a tension test, a compression test, and a bending test of the nano material specimen, and the lower jig clamps one side of a lower portion of the nano material specimen and is detachably coupled to the stage unit so that the lower jig is capable of being replaced with another one for each of a tension test, a compression test, and a bending test of the nano material specimen.

7. The nano material testing apparatus of claim 1, further comprising a humidity chamber configured to seal the nano material specimen and the jig unit clamping the nano material specimen.

8. A method for testing a material using a nano material testing apparatus including a testing unit including an actuator coupled to an upper portion of a main frame and generating displacement of a nano material specimen and a load cell connected to the actuator, a jig unit connected to the testing unit and comprising an upper jig that clamps one side of an upper portion of the nano material specimen and a lower jig that is located below the upper jig and clamps one side of a lower portion of the nano material specimen, a stage unit enabling the lower jig to be moved in a multi-axis direction, a first alignment unit comprising a first camera, which provides an image of a front surface of the nano material specimen and allows alignment in a direction of the front surface of the nano material specimen to be checked, a second alignment unit comprising a second camera, which provides an image of side surfaces of the nano material specimen and allows alignment in a direction of the side surfaces of the nano material specimen to be checked, a specimen auxiliary fixing device selectively clamping the other side of the nano material specimen, and a load cell protection device that is selectively connected to the upper jig by moving forward/backward, the method comprising:

mounting the nano material specimen on the specimen auxiliary fixing device, wherein the mounting is performed by a worker;

moving the stage unit to move the lower jig to the specimen auxiliary fixing device and then, moving the nano material specimen to the lower jig, mounting the nano material specimen on the lower jig, and moving the stage unit so that the lower jig is moved to be below the upper jig, wherein the moving, the moving, the mounting, and the moving are performed by the worker;

checking alignment of the nano material specimen using the first alignment unit and the second alignment unit to adjust a position of the nano material specimen, wherein the checking and the adjusting are performed by the worker;

mounting the nano material specimen on the upper jig in a state in which the load cell protection device is connected to the upper jig, wherein the mounting is performed by the worker;

separating the load cell protection device from the upper jig and then carrying out a test by moving the actuator, wherein the separating and the carrying out is performed by the worker; and measuring a change in the nano material specimen using information received from the first alignment unit, the second alignment unit, and the load cell during a test, wherein the measuring is performed by a controller.

\* \* \* \* \*